(12) United States Patent
Knowles et al.

(10) Patent No.: US 11,020,534 B2
(45) Date of Patent: Jun. 1, 2021

(54) FIXED DOSE INJECTOR PEN

(71) Applicant: Shaily Engineering Plastics Limited, Gujarat (IN)

(72) Inventors: Stephen Knowles, Datchet (GB); Michal Uhman, Datchet (GB)

(73) Assignee: Shaily Engineering Plastics Limited, Gujarat (IN)

( * ) Notice: Subject to any disclaimer, the term of this patent is extended or adjusted under 35 U.S.C. 154(b) by 180 days.

(21) Appl. No.: 16/382,983

(22) Filed: Apr. 12, 2019

(65) Prior Publication Data

US 2020/0306451 A1    Oct. 1, 2020

(30) Foreign Application Priority Data

Mar. 25, 2019 (GB) ..................... 1904051

(51) Int. Cl.
*A61M 5/315* (2006.01)
*A61M 5/20* (2006.01)

(52) U.S. Cl.
CPC ...... *A61M 5/3156* (2013.01); *A61M 5/31551* (2013.01); *A61M 5/31593* (2013.01);
(Continued)

(58) Field of Classification Search
CPC ............ A61M 5/3156; A61M 5/31551; A61M 5/31593; A61M 5/2033; A61M 5/31541;
(Continued)

(56) References Cited

U.S. PATENT DOCUMENTS 6,235,004 B1    5/2001   Steenfeldt-Jensen et al.
6,582,404 B1 *  6/2003   Klitgaard .......... A61M 5/31553
                                                            604/181

(Continued)

FOREIGN PATENT DOCUMENTS

EP    1681070 A1    7/2006
EP    2351591 A1    8/2011
(Continued)

OTHER PUBLICATIONS

International Search Report (Form PCT/ISA/210) for International PCT Application No. PCT/EP2020/058428, issued by the European Patent Office (EPO), dated Jun. 26, 2020, including Notification of Transmittal and annex, 4 pages.
(Continued)

*Primary Examiner* — Nathan R Price
*Assistant Examiner* — Luke J. Efta
(74) *Attorney, Agent, or Firm* — Kilyk & Bowersox, P.L.L.C.

(57) ABSTRACT

A fixed dose injector pen is provided that includes a transmission element that is rotated to set and deliver a dose of a drug from a multi-dose cartridge. A circular ratchet defines a small number of engagement positions around its circumference and selectively transmits the rotation of the transmission element to a piston rod driver. The circular ratchet transmits the rotation of the transmission element to the piston rod driver only when the transmission element is rotated in a dose delivery direction, and only if the transmission element has previously been rotated in an opposite, dose setting direction through an angle sufficient to reach one of the engagement positions. An axially moving injector element can be used to drive rotation of the transmission element via a helical coupling. When the piston rod has advanced to a predetermined axial position, a last dose lock-out mechanism maintains the circular ratchet in engagement.

10 Claims, 5 Drawing Sheets

(52) U.S. Cl.
CPC ....... *A61M 5/2033* (2013.01); *A61M 5/31541* (2013.01); *A61M 5/31553* (2013.01); *A61M 5/31585* (2013.01)

(58) Field of Classification Search
CPC .......... A61M 5/31553; A61M 5/31585; A61M 5/315; A61M 5/31535; A61M 5/31511; A61M 5/31526; A61M 5/31555
See application file for complete search history.

(56) References Cited

U.S. PATENT DOCUMENTS

| | | |
|---|---|---|
| 6,585,698 B1 | 7/2003 | Packman et al. |
| 7,517,334 B2 | 4/2009 | Jacobs et al. |
| RE41,956 E | 11/2010 | Klitgaard et al. |
| 8,771,237 B2 | 7/2014 | Markussen |
| 9,724,478 B2 | 8/2017 | Markussen |
| 10,300,207 B2 | 5/2019 | Newton et al. |
| 2004/0127858 A1 | 7/2004 | Bendek et al. |
| 2012/0245532 A1* | 9/2012 | Frantz ............... A61M 5/31561 604/211 |
| 2013/0046248 A1 | 2/2013 | Raab |
| 2016/0151577 A1 | 6/2016 | Newton et al. |
| 2017/0209651 A1 | 7/2017 | Moser et al. |

FOREIGN PATENT DOCUMENTS

| | | | |
|---|---|---|---|
| EP | 3006068 A1 | 4/2016 | |
| TW | 201600134 A | 1/2016 | |
| WO | 2004030730 A2 | 4/2004 | |
| WO | 2004030730 A3 | 4/2004 | |
| WO | 2008148539 A1 | 12/2008 | |
| WO | 2013076026 A1 | 5/2013 | |
| WO | 2014122206 A1 | 8/2014 | |
| WO | 2016038445 A1 | 3/2016 | |
| WO | 2018/041899 A1 | 3/2018 | |
| WO | WO-2018041899 A1 * | 3/2018 | .......... A61M 5/3155 |
| WO | 2018146589 A2 | 8/2018 | |

OTHER PUBLICATIONS

Written Opinion of the International Searching Authority (Form PCT/ISA/237), for International PCT Application No. PCT/EP2020/058428, issued by the European Patent Office (EPO), dated Jun. 26, 2020, including Information on Search Strategy, 6 pages.

Examination Report issued from the United Kingdom Intellectual Property Office dated Oct. 9, 2020, for corresponding application No. GB1904051.8.

* cited by examiner

FIXED DOSE INJECTOR PEN

CROSS-REFERENCE TO RELATED APPLICATION

The present application claims priority to United Kingdom Patent Application No. 1904051.8 filed on Mar. 25, 2019, the disclosure of which is expressly incorporated by reference herein in its entirety.

FIELD OF THE INVENTION

Technical Field

An injector pen provides a mechanism for setting a predetermined dose of a drug and delivering that dose to a patient from a drug cartridge. The drug cartridge typically contains multiple doses of the drug in a chamber and the injector pen comprises a piston rod that is progressively extended from the pen to deliver doses from the chamber, the piston rod moving through a distance that determines the volume of the dose delivered. The pen mechanism prevents delivery of the drug if only a partial dose has been set.

BACKGROUND TO THE INVENTION

Many designs of injector pen are known. Typically the pen has cylindrical pen body and a dose selector. In a dose setting phase of operation the user moves the dose selector axially and/or rotationally relative to the pen body to a position that determines the dose for delivery, then in a drug delivery phase of operation the user pushes the dose selector axially into the pen body to deliver the dose. The pen further comprises means for attaching a drug cartridge to the pen; and a piston rod, which moves along the axis of the pen to act on the piston of the drug cartridge. In the drug delivery phase, the proximal end of the pen is pressed, e.g. by the user's thumb, to push the dose selector into the pen body. During drug delivery, a drive mechanism within the pen body converts the movement of the dose selector into axial movement of the piston rod through a distance suitable to deliver the required dose from the cartridge. The distance moved by the piston rod is thus determined by the distance moved by the dose selector but the two distances need not be equal. On each use of the pen to deliver the drug from the same cartridge, the piston rod advances further along the axis. The piston rod does not move axially during the dose setting phase.

In many cases, it is desirable that the dose of the drug to be delivered by an injector pen should not be freely selectable by the user but should be a fixed volume, determined in advance to match a prescribed dose. The user should be prevented from setting and delivering only a partial dose.

Since the injector pen can deliver multiple doses of drug from a single cartridge, after repeated uses the cartridge may reach a state where it has less than a full dose of the drug remaining. In that case, regulations typically require that the pen should be automatically locked to prevent further use. This function is referred to as "last dose lock-out".

SUMMARY OF THE INVENTION

The invention provides a fixed dose injector pen, as defined in claim 1.

Preferred but non-essential features of the invention are defined in the dependent claims.

In this specification, the word "drug" is used to describe any fluid substance that is to be delivered by the pen in measured doses. It will typically be a biologically active substance that is injected into the body of a human or animal subject, e.g. for medicinal or cosmetic purposes. However, the invention could be used in other applications where it is desired to dispense fixed quantities of a substance.

BRIEF DESCRIPTION OF THE DRAWINGS

The present invention can be even more fully understood with the reference to the accompanying drawings which are intended to illustrate, not limit, the present invention.

DETAILED DESCRIPTION OF THE INVENTION

Figure 1A:
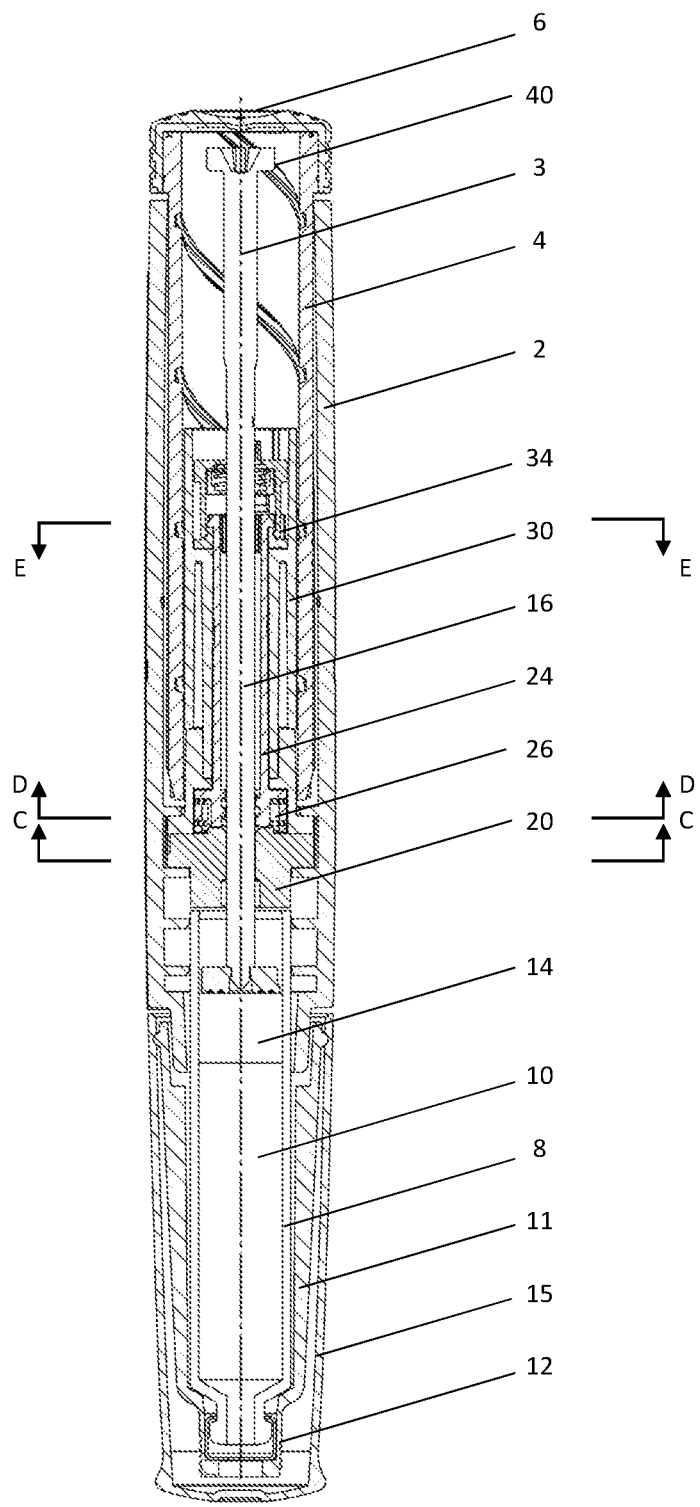
FIGS. 1a and 1b are longitudinal cross sections through an injector pen according to the invention, with the injector element in fully inserted and fully withdrawn positions, respectively.
Figure 1B:
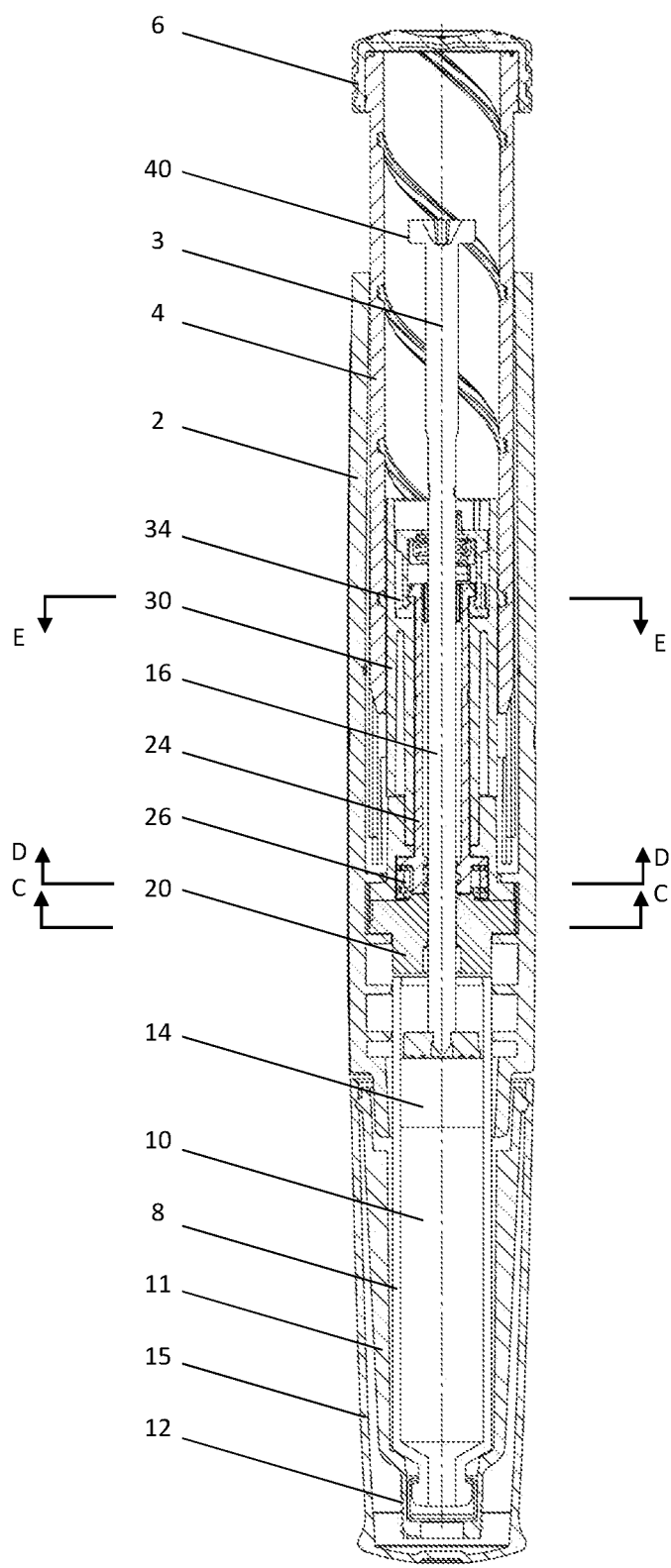

An injector pen according to a preferred embodiment of the injection is illustrated in FIGS. 1 to 6. It comprises a generally cylindrical, hollow pen body 2 centred on a longitudinal axis 3 of the pen. An injector element 4 is mounted in the pen body 2 and is configured to slide axially relative to the pen body 2 for setting or delivering a dose of a drug. Relative rotation between the pen body 2 and the injector element 4 is prevented by complementary features such as a pair of flats or a key and keyway (not illustrated). A proximal end of the injector element 4 projects from a proximal end of the pen body 2 to form an injector button 6 that can be gripped manually by the user to withdraw it from the pen body 2 (FIG. 1b) or push it back into the pen body 2 (FIG. 1a).

A drug cartridge 8 is mounted on a distal end of the pen body 2. The drug cartridge 8 comprises a chamber 10 that contains multiple doses of a drug for injection into a patient. The drug cartridge 8 is enclosed by a cover 11 that provides connection means for retaining the drug cartridge 8 in the pen body 2. The cover 11 further comprises a thread 12 or other means for mounting a hypodermic needle (not illustrated) in fluid communication with the chamber 10. A piston 14 in the chamber 10 can be pushed along the axis 3 of the pen to force doses of the drug out of the chamber 10 via the needle. The distal end of the pen is covered by a removable pen cap 15 when not in use.

The injector pen comprises a piston rod 16 that lies along the axis 3, partly within the pen body 2 and partly extending from the distal end of the pen body 2 to penetrate the chamber 10 of an attached drug cartridge 8. By moving along the axis 3 in a direction from the proximal end towards the distal end of the pen body (the "first axial direction"), the piston rod 16 pushes the piston 14 along the axis 3 to deliver a dose of the drug from the chamber 10.

In this embodiment of the invention, the piston rod 16 is solid in cross-section and carries a helical thread 17 on its outer surface. The piston rod 16 also comprises an opposing pair of flats 18 extending along its length, as a result of which the thread 17 is discontinuous.

Figure 3:
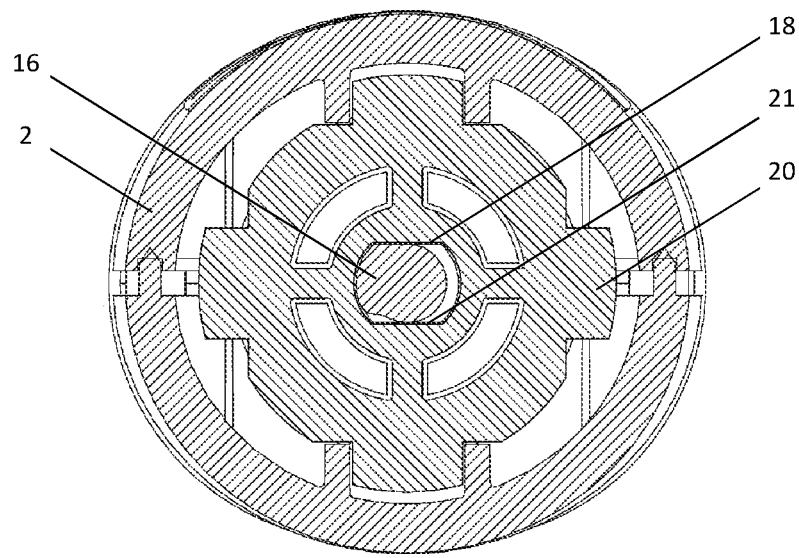
FIG. 3 is a radial cross section through the piston rod guide of the injector pen, taken on plane C-C of FIG. 1.
Figure 4:
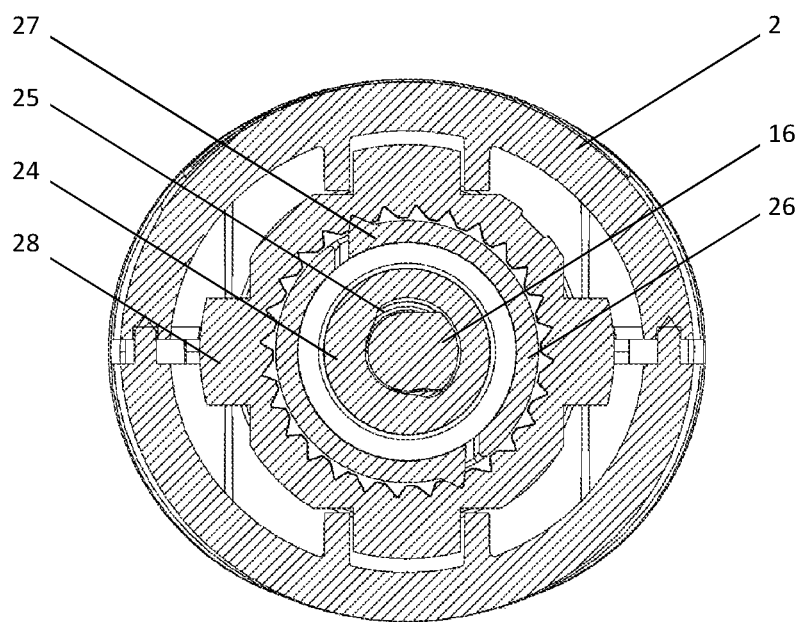
FIG. 4 is a radial cross section through a first circular ratchet of the injector pen, taken on plane D-D of FIG. 1.

A piston rod guide 20 is secured within the pen body 2 such that it cannot rotate. The piston rod guide 20 is mounted concentrically with the piston rod 16 and comprises an opposing pair of internal flats 21 that engage the flats 18 of the piston rod 16 to allow the piston rod 16 to slide through the piston rod guide 20 but to prevent the piston rod 16 rotating (FIG. 3). It will be apparent that methods of engagement other than flats 18,21 could be used to achieve a similar sliding but non-rotating coupling between the piston rod 16 and the piston rod guide 20, e.g. a pin on the guide 20 acting in a keyway of the piston rod 16; or the piston rod 16 and the piston rod guide 20 having alternative complementary, non-circular cross sections.

Axial movement of the piston rod 16 is driven by a piston rod driver 24 that is mounted coaxially in the pen body 2 so as to be capable of rotation but not axial translation. A bore in the piston rod driver 24 comprises an internal thread 25 that engages the external thread 17 on the piston rod 16. Since the piston rod 16 is prevented from rotating by the piston rod guide 20, rotation of the piston rod driver 24 about the threaded coupling drives the piston rod 16 to slide along the axis 3. A first circular ratchet 26 (FIG. 4) permits rotation of the piston rod driver 24 only in a first rotary direction, which is the direction that causes the piston rod 16 to advance in the first axial direction and deliver a dose of the drug from the cartridge 8. In the illustrated embodiment, the first circular ratchet 26 comprises ratchet arms 27 and a circular pawl 28. The ratchet arms 27 are formed integrally with the piston rod driver 24 and extend outwards from it. The pawl 28 is formed as a discrete element and fixedly mounted in the pen body 2. It is apparent that the ratchet 26 could take other forms: for example, the ratchet arms 27 could be provided by a discrete element attached to the piston rod driver 24 and/or the circular pawl 28 could be formed integrally with the pen body 2 or the piston rod guide 20.

A cylindrical transmission element 30 is mounted concentrically in the pen body 2, outside the piston rod driver 24 and inside the injector element 4. The transmission element 30 is able to rotate about the axis 3 but is constrained so it cannot move along the axis 3. A male helical thread 31 projects from an outer cylindrical surface of the transmission element 30 and engages a female helical groove 32 in an inner cylindrical surface of the injector element 4. The helical coupling formed by the thread 31 and the groove 32 is non-self-locking so that sliding the injector element 4 axially in either direction causes rotation of the transmission element 30. It is apparent that the helical coupling can be achieved in alternative ways, e.g. by interchanging the male thread 31 and the female groove 32, and that the male component need not be a complete thread but could comprise small projections that travel along the groove 32. In the illustrated embodiment the thread 31 and the groove 32 have two starts but a different number of starts could be chosen.

Figure 5:
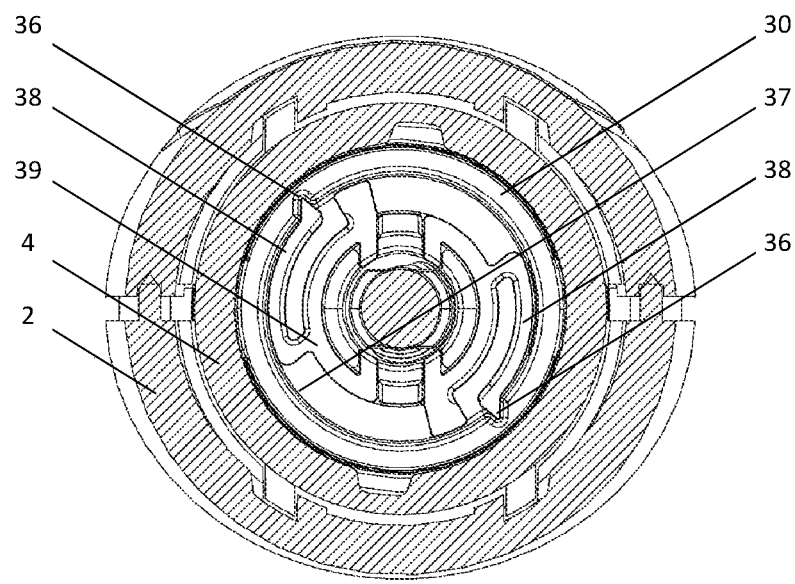
FIG. 5 is a radial cross section through a second circular ratchet of the injector pen, taken on plane E-E of FIG. 1.
Figure 6:
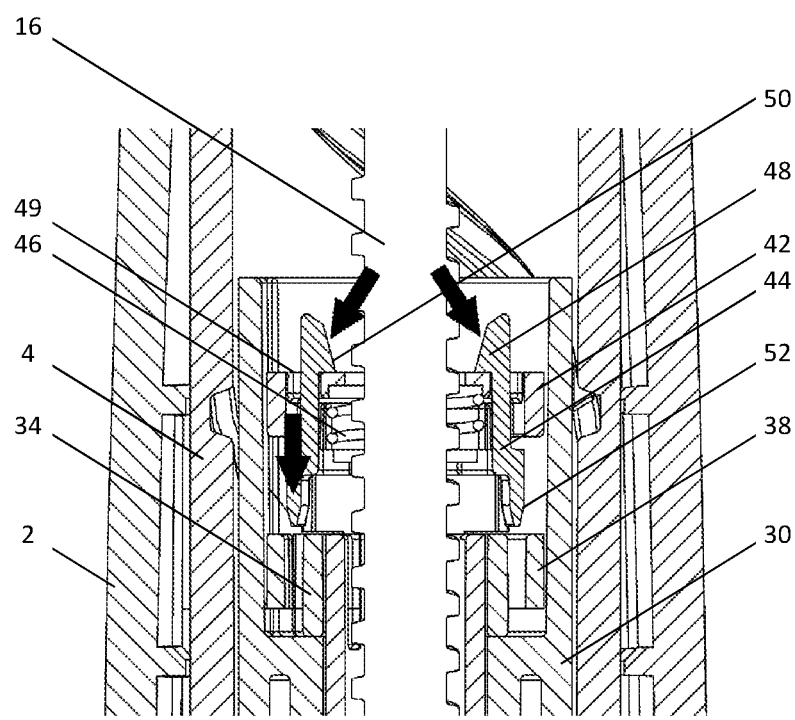
FIG. 6 is a longitudinal cross section through the last dose lock-out mechanism of the injector pen of FIG. 1.

A second circular ratchet 34 is mounted between the transmission element 30 and the piston rod driver 24 for selectively transmitting the rotation of the transmission element 30 to the piston rod driver 24. As seen in FIG. 5, the second circular ratchet 34 comprises two resilient ratchet arms 38 that extend outwards from the piston rod driver 24 and a corresponding pair of diametrically opposed, axial grooves 36 formed in an inner cylindrical surface 37 of the transmission element 30. In the illustrated embodiment of the invention, the ratchet arms 38 are part of a discrete ratchet element 39 that is fixed to the piston rod driver 24 but it is apparent that in alternative embodiments they could be formed integrally with the piston rod driver 24. Each groove 36 has an asymmetric cross section, with one wall at a shallow angle and the opposing wall at a steep angle, and the tip of each ratchet arm 38 has a complementary shape that can lodge against the steeper wall of the groove 36 during rotation of the transmission element 30 in the first rotary direction, but can ride over the shallow wall of the groove 36 during rotation of the transmission element 30 in the opposite direction (hereafter the "second rotary direction"). It is apparent that axially extending grooves 36 are not the only recess-like structure that is capable of selectively engaging the ratchet arms 38: for example, the inner cylindrical surface 37 could be provided with suitably shaped pits or circumferentially-facing steps to achieve a similar function.

When the injector element 4 is withdrawn from the pen body 2 in a dose setting phase of operation, it causes the transmission element 30 to rotate in the second rotary direction. Then the tips of the ratchet arms 38 ride over the ratchet grooves 36 and do not transmit the rotation to the piston rod driver 24. The first circular ratchet 26 also prevents rotation of the piston rod driver 24 in the second rotary direction that might result from frictional contact between the ratchet arms 38 and the inner cylindrical surface 37.

When the injector element 4 is pushed into the pen body 2 in a dose delivery phase of operation, it causes the transmission element 30 to rotate in the first rotary direction. Then the ratchet grooves 36 can firmly engage the tips of the ratchet arms 38 and transmit the rotation to the piston rod driver 24, which in turn drives the piston rod 16 to advance along the axis 3 and deliver a dose from the drug cartridge 8.

It should be noted that the ratchet arms 38 can engage the grooves 36 only at certain engagement positions around the circumference of the transmission element 30. In between those engagement positions, the ratchet arms 38 slide freely over the inner cylindrical surface 37 of the transmission element 30, when rotated in either direction.

When the injector pen has completed delivery of a dose of the drug, the injector element 4 has been pushed fully into the pen body 2 to reach its final position, as shown in FIG. 1a, and the transmission element 30 has been rotated in the first rotary direction with the second circular ratchet 34 engaged. If the injector element 4 is now withdrawn to set a new dose for delivery, it causes the transmission element 30 to rotate in the second rotary direction with the ratchet arms 38 sliding over its inner surface 37. It can be seen from FIG. 5 that the transmission element 30 needs to rotate through 180 in the second rotary direction before the ratchet arms 38 can once again engage in the ratchet grooves 36. If the rotation is reversed before reaching 180°, the arms 38 will not engage and the rotation will not be transferred to the piston rod driver. If the dose-setting rotation in the second rotary direction exceeds 180°, the ratchet arms 38 will first ride over the grooves 36 and continue sliding over the inner surface 37 until, when the direction is subsequently reversed to deliver a drug, the arms 38 slide back and re-engage the grooves 36 at the 180° engagement position. From there, continued rotation of the transmission element 30 in the first rotary direction will drive rotation of the piston rod driver 24 through 180° until the injector element 4 reaches the final position again.

By choosing the thread 17 of the piston rod 16 to have a suitable pitch, it can be arranged that rotation of the piston rod driver 24 through 180° results in delivery of the desired fixed dose from the cartridge 8. Rotation of the transmission element 30 and the piston rod driver 24 through 180° corresponds to movement of the injector element 4 through a predetermined axial distance to the position shown in FIG. 1b. The predetermined distance depends on the pitch of the helical coupling 31,32. The injector element 4 is preferably constrained to prevent it moving through an axial distance significantly greater than the predetermined distance.

Injector pens according to preferred embodiments of the invention also include a last dose lock-out feature, which prevents the pen being used to set and deliver a dose if the drug cartridge 8 contains less than the predetermined fixed dose. As the pen is repeatedly re-used, the piston rod 16 advances along the axis 3 to displace doses of the drug from the cartridge 8. The position of the piston rod 16 is thus a measure of the quantity of drug remaining in the cartridge 8.

Figure 2:
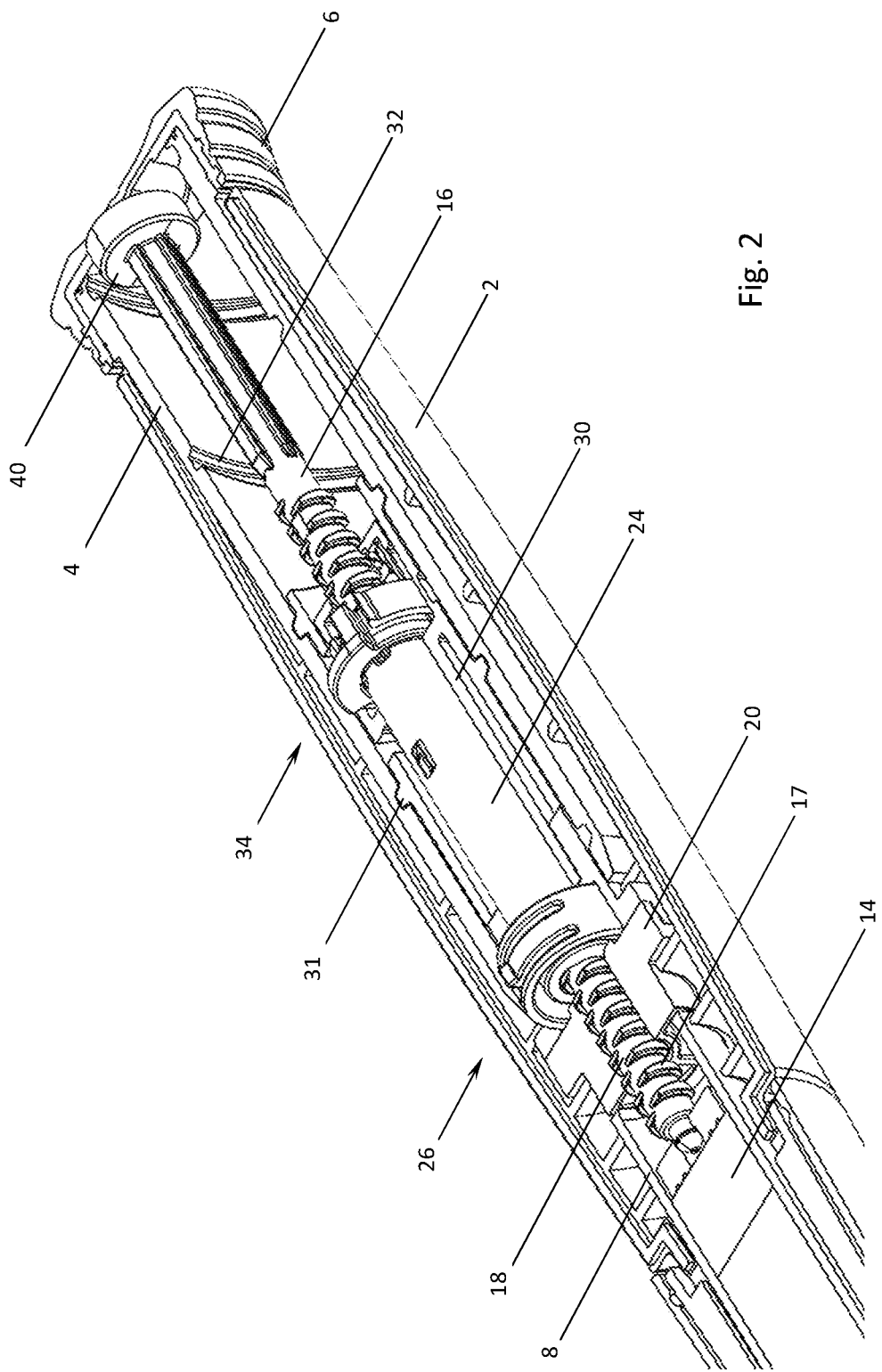
FIG. 2 is a cut-away perspective view of part of the injector pen of FIG. 1.

The piston rod 16 comprises an enlarged head 40 at its proximal end. FIGS. 1 and 2 show the pen at an early stage, when the piston rod 16 is at or near its starting position and fully extended in the proximal direction. With the delivery of multiple doses, the piston rod 16 advances in the distal direction until the head 40 of the piston rod 16 approaches the last dose lock-out mechanism shown in FIG. 6. The last dose lock-out mechanism comprises a collar 42 and a locking element 44 that surround the piston rod 16 within the transmission element 30. The collar 42 is fixed to the second circular ratchet 34. The locking element 44 can move axially relative to the collar 42 and is urged to move in the first axial direction by a spring 46 mounted between the collar 42 and the locking element 44. However, the locking element 44 is prevented from moving by a pair of hooks 48 that engage a proximal surface 49 of the collar 42.

As the piston rod 16 advances, its head 40 comes into contact with inclined cam surfaces 50 of the hooks 48. Continued advancement of the head 40 in the first axial direction forces the hooks 48 apart, as shown by the upper pair of black arrows in FIG. 6, until the hooks 48 disengage from the proximal surface 49. Now the spring 46 drives the locking element 44 to move in the first axial direction, as shown by the lower black arrow in FIG. 6, so that locking wedges 52 are pushed into positions immediately radially inwards from the ratchet arms 38 of the second circular ratchet 34. It is recalled that, because the piston rod 16 is advancing, the second circular ratchet 34 must be engaged. Its ratchet arms 38 are therefore flexed outwards to enter the grooves 36 of the transmission element 30, leaving spaces behind them for insertion of the wedges 52.

When a subsequent attempt is made to withdraw the injector element 4 and rotate the transmission element 30 in the second rotary direction to set a new dose, the wedges 52 prevent the ratchet arms 38 disengaging from the grooves 36 so the transmission element 30 remains rotationally locked to the piston rod driver 24. The first circular ratchet 26 prevents rotation of the piston rod driver 24 in the second rotary direction. In turn this prevents rotation of the transmission element 30 to set a new dose so the pen becomes inoperable.

As will be apparent, the length of the piston rod 16 should be chosen so that its head 40 activates the last dose lock-out mechanism on or near completion of delivery of the final full dose in the cartridge 8.

In the preferred embodiment of the invention there are two engagement positions of the second circular ratchet 34, spaced 180° apart. However, in alternative embodiments there could be a different number n of engagement positions, equally spaced at 360/n degrees apart. Preferably $1 \leq n \leq 4$.

An alternative configuration of the piston rod driver 24 and the piston rod guide 20 is possible, which comprises a threaded coupling between the piston rod guide 20 and the piston rod 16, and a sliding, co-rotating coupling between the piston rod 16 and the piston rod driver 24. For example, the piston rod driver 24 may comprise a pair of internal flats to engage the external flats 18 of the piston rod 16 and force the piston rod 16 to co-rotate with the piston rod driver 24. Thereby, rotation of the piston rod 16 within the threaded coupling of the piston rod guide 20 drives the piston rod 16 to advance along the axis 3.

Several variants of the illustrated embodiments have been described above. In the absence of any contrary statement, each variant can be adopted independently of the others and they can be used in any combination.

The entire contents of all references cited in this disclosure are incorporated herein in their entireties, by reference. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether such ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. An injector pen, comprising:
 a piston rod guide;
 a piston rod driver configured to rotate without axial movement relative to the piston rod guide;
 a piston rod coupled to the piston rod driver and to the piston rod guide such that rotation of the piston rod driver drives axial movement of the piston rod relative to the piston rod guide;
 a first circular ratchet that constrains the piston rod driver to rotate only in a first rotary direction, which drives the piston rod to move in a first axial direction;
 a transmission element configured to rotate without axial movement, relative to the piston rod guide, in the first rotary direction or in a second, opposite rotary direction; and
 a second circular ratchet that selectively engages the transmission element with the piston rod driver such that:
  rotation of the transmission element in the second rotary direction is not transmitted to the piston rod driver; and
  rotation of the transmission element in the first rotary direction is transmitted to the piston rod driver only if the transmission element has previously been rotated in the second rotary direction through a predetermined angle that is sufficient to permit engagement of the second circular ratchet.

2. An injector pen according to claim 1, wherein the second circular ratchet comprises n engagement positions equally spaced around its circumference; wherein the predetermined angle is 360/n degrees; and wherein rotation of the piston rod driver through 360/n degrees advances the piston rod by a distance required to deliver a predetermined dose of a drug from the pen.

3. An injector pen according to claim 2, wherein n=2.

4. An injector pen according to claim 2, wherein the second circular ratchet comprises one or more ratchet arms and one or more recesses, each engagement position of the second circular ratchet being defined by an angular position at which a ratchet arm is capable of engaging in a recess, wherein the cross-sectional shapes of the recess and the ratchet arm are such that the ratchet arm rides over the recess when the transmission element is rotated in the second rotary direction but the ratchet arm engages the recess when the transmission element is rotated in the first rotary direction.

5. An injector pen according to claim 4, wherein the or each recess is an axial groove formed in an inner circumferential surface of the transmission element and the or each ratchet arm extends outwards from the piston rod driver.

6. An injector pen according to claim 4, further comprising a last dose lock-out mechanism, whereby, when the piston rod moves to a predetermined axial position, the second circular ratchet is prevented from disengaging and the first and second circular ratchets in combination prevent the transmission element being rotated in the second rotary direction.

7. An injector pen according to claim 6, wherein the last dose lock-out mechanism comprises wedges that can be driven behind the ratchet arms of the second circular ratchet to prevent the ratchet arms disengaging from the recesses of the second circular ratchet.

8. An injector pen according to claim 1, further comprising:
  an injector element configured to move axially without rotation, relative to the piston rod guide, in the first axial direction or in a second, opposite axial direction; and
  a helical coupling between the injector element and the transmission element, configured such that axial movement of the injector element in the first or the second axial direction causes rotation of the transmission element respectively in the first or the second rotary direction.

9. An injector pen according to claim 1, comprising a threaded coupling between the piston rod and the piston rod driver, and a non-rotary coupling between the piston rod and the piston rod guide, whereby rotation of the piston rod driver about the threaded coupling drives the piston rod to move axially, without rotation, relative to the piston rod guide.

10. An injector pen according to claim 1, comprising a co-rotating coupling between the piston rod and the piston rod driver, and a threaded coupling between the piston rod and the piston rod guide, whereby rotation of the piston rod driver forces the piston rod to rotate, and rotation of the piston rod within the threaded coupling of the piston rod guide drives the piston rod to move axially.

* * * * *